United States Patent
Kapfermann et al.

(10) Patent No.: US 9,486,277 B2
(45) Date of Patent: Nov. 8, 2016

(54) RESECTOSCOPE

(71) Applicant: OLYMPUS WINTER & IBE GMBH, Hamburg (DE)

(72) Inventors: Nils Kapfermann, Hamburg (DE); Christian Brockmann, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 322 days.

(21) Appl. No.: 13/940,887

(22) Filed: Jul. 12, 2013

(65) Prior Publication Data

US 2014/0018799 A1    Jan. 16, 2014

(30) Foreign Application Priority Data

Jul. 12, 2012 (DE) .......................... 10 2012 023 275

(51) Int. Cl.
*A61B 18/18* (2006.01)
*A61B 18/14* (2006.01)
*A61B 1/00* (2006.01)
*A61B 18/00* (2006.01)

(52) U.S. Cl.
CPC ......... *A61B 18/1485* (2013.01); *A61B 18/149* (2013.01); *A61B 1/00087* (2013.01); *A61B 2018/00178* (2013.01)

(58) Field of Classification Search
CPC .......... A61B 2018/00172; A61B 2018/00178; A61B 2017/00269; A61B 17/320016; A61B 1/00121; A61B 1/00124
See application file for complete search history.

(56) References Cited

U.S. PATENT DOCUMENTS

| | | | | |
|---|---|---|---|---|
| 4,919,131 | A * | 4/1990 | Grossi | A61B 18/14 606/46 |
| 5,007,907 | A * | 4/1991 | Nishigaki et al. | 606/46 |
| 6,105,581 | A * | 8/2000 | Eggers et al. | 128/898 |
| 6,322,494 | B1 * | 11/2001 | Bullivant et al. | 600/104 |
| 6,746,395 | B2 * | 6/2004 | Brommersma et al. | 600/105 |
| 6,974,458 | B2 * | 12/2005 | Muller | A61B 18/1485 439/224 |
| 9,001,471 | B2 * | 4/2015 | Miller et al. | 360/294.4 |
| 2006/0058580 | A1 | 3/2006 | Reichenbach et al. | |

FOREIGN PATENT DOCUMENTS

DE    10 2004 045 337 A1    4/2006
WO    WO 2011/134625 A1    11/2011

OTHER PUBLICATIONS

Germany Examination Report dated Mar. 26, 2013 in Germany Patent Application No. 10 2012 0230275.6 w/Appendix.

* cited by examiner

*Primary Examiner* — Ronald Hupczey, Jr.
(74) *Attorney, Agent, or Firm* — Oliff PLC

(57) ABSTRACT

A resectoscope includes an electrode arrangement having at least one electrode and being connected to a contact at a proximal end region of the electrode arrangement; a retaining body mounted on the resectoscope that is movable in the direction of movement of the electrode arrangement and includes an electrode mounting for accommodating the end region of the electrode arrangement; and a cable with a plug body for fixing to the retaining body while making contact with the contacts. The retaining body has a plug receptacle for fixing the plug body by an insertion movement aligned at right angles to the direction of movement of the electrode arrangement. In the position which is reached at the end of the insertion movement, the plug body can be turned into an end position where it is blocked by the plug receptacle against a movement in the opposite direction to the insertion movement.

10 Claims, 6 Drawing Sheets

RESECTOSCOPE

BACKGROUND

The invention relates to a resectoscope.

Resectoscopes have a manually movable retaining body, by means of which an electrode, which, when HF is applied, can remove body tissue, can be moved in a longitudinal direction. A main area of application is prostate resection, in which the prostate tissue is cut in longitudinal movements away from the urethra with a cutting loop to which HF is applied. Apart from this application in urology, further applications of resectoscopes are known, primarily in gynecology for working in the uterus.

A resectoscope of the kind mentioned in the introduction is disclosed in U.S. Pat. No. 4,919,131 A. This publication is concerned mainly with the connection between the cable carrying the HF voltage from the outside and the electrode arrangement. A plug body, which connects a conductor in the cable to a conductor in the electrode arrangement, is presented. The plug body can be plugged into a plug receptacle in the main body for fixing and connecting purposes.

SUMMARY

With this known design, the plug body is pushed into the plug receptacle with only a linear sliding movement and held there by friction. This retention is uncertain, particularly when the cable is pulled during rough operation. This can then easily lead to a disengagement or loosening of the plug body and therefore to a deterioration or interruption of the contact. Connection problems are, however, very serious with high-frequency operation, as they can lead to burning of the contacts. This also jeopardizes reliable operation.

The object of the present invention consists in improving the connection reliability of a resectoscope of the kind mentioned in the introduction.

This object is achieved with the characteristics of the various embodiments.

According to an exemplary embodiment, the plug body is first inserted into the plug receptacle and, in the position reached at the end of the insertion movement, is then rotated into an end position in which it is blocked by the plug receptacle against a withdrawal movement. The plug body is thereby secured. A simple pull on the cable is no longer sufficient to loosen the plug body. Rather, a deliberate actuation which first requires a turning movement and then a pulling movement is necessary for this purpose. It is therefore ensured that a disengagement and loosening of the plug body can only take place intentionally and not unintentionally when using the resectoscope. This significantly increases the operational safety.

An exemplary embodiment describes a specific physical embodiment of the design in order to achieve the object according to the invention. According to this, the plug body is turned by means of the rotatable mounting of a cylinder formed on the plug body in a corresponding hollow cylinder in the retaining body. However, the plug body has a flattened periphery and, in a particular angular position, can be inserted from the outside into the region of the cylinder or removed therefrom through a slot. When the plug body is inserted through the slot into the region of the cylinder and then turned, it can no longer pass through the slot and is therefore secured by interlocking.

Preferably, according to an exemplary embodiment, the axis of the cylinder is aligned parallel to the direction of movement of the electrode arrangement. This enables a design which can be logically operated, in which the plug body can be inserted laterally through the slot at right angles to the direction of movement of the electrode arrangement.

Preferably, according to an exemplary embodiment, a latching device, which secures the plug body in the retaining body in its end position, is provided. This provides an additional safeguard against unintentional operation.

Preferably, according to an exemplary embodiment, the electrode mounting is formed in the plug body. This results in a direct connection of the electrode arrangement by means of the plug body, as in the design of the publication mentioned in the introduction. There are also advantages with regard to the contact quality and fault tolerance.

Advantageously, according to an exemplary embodiment, the electrode arrangement is designed in the form of a hole in the cylindrical part of the plug body. It could lie on the axis of rotation of the cylinder, which would also definitely have advantages, but it is advantageously displaced with respect to the axis of rotation of the cylinder towards the guide hole of the retaining body, by means of which the latter is movably guided in a longitudinal direction. As is known, there are always major problems with resectoscopes with the distance of the electrode mounting from the guide hole. Too great a distance must be compensated for by constructively difficult deviations of guide channels. The above described embodiment provides a remedy for this.

BRIEF DESCRIPTION OF THE DRAWINGS

The invention is shown by way of example and schematically in the drawings. In the drawings.

DETAILED DESCRIPTION OF THE EMBODIMENTS

Figure 1:
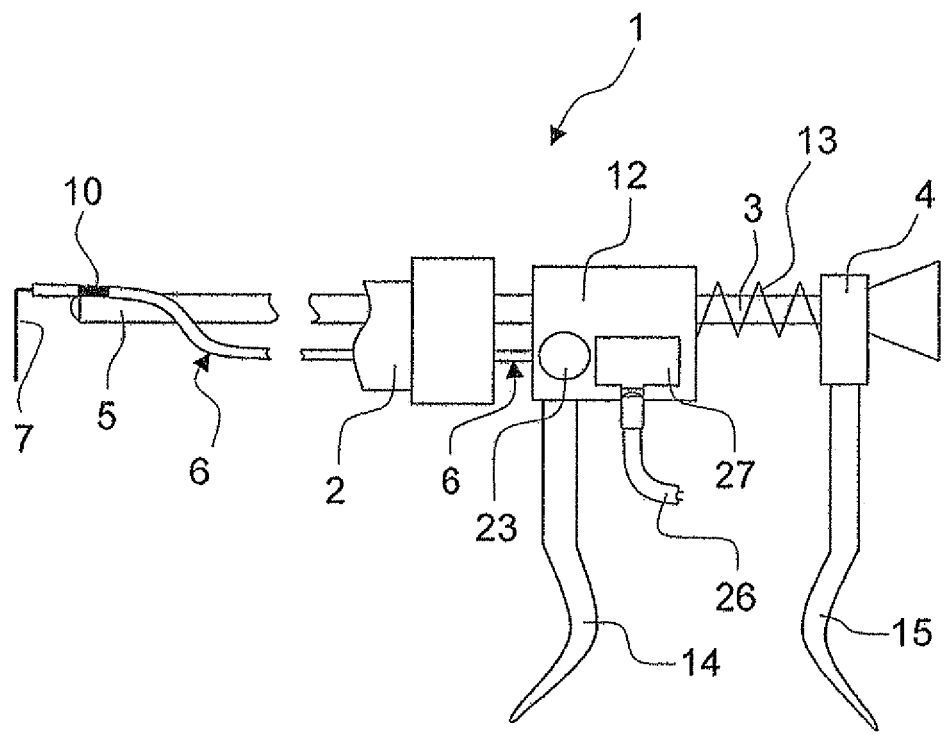
FIG. 1 shows a side view of a resectoscope according to the invention having a retaining body which can be moved in a longitudinal direction.

FIG. 1 shows a resectoscope 1 in side view. The resectoscope 1 corresponds substantially to the generally prevailing basic design. This includes a shaft tube 2, over which a guide tube 3, to the proximal end of which a guide plate 4 is fixed, projects in a proximal direction. A rod-shaped lens 5, by means of which the operating region can be observed distally from the lens 5, is inserted through said plate and the guide tube 3 into the shaft tube 2.

In addition to the lens 5, an electrode arrangement 6 is also arranged in the shaft tube 2. The electrode arrangement is thin and elongated and is provided with an insulating sleeve over its length. In the distal end region, the electrode arrangement supports an electrode 7, which can be designed in the form of a loop as is usual with resectoscopes. Further, a return electrode 10 is arranged in the distal end region, so that bipolar operation is possible with two electrodes 7 and 10.

Figure 3:
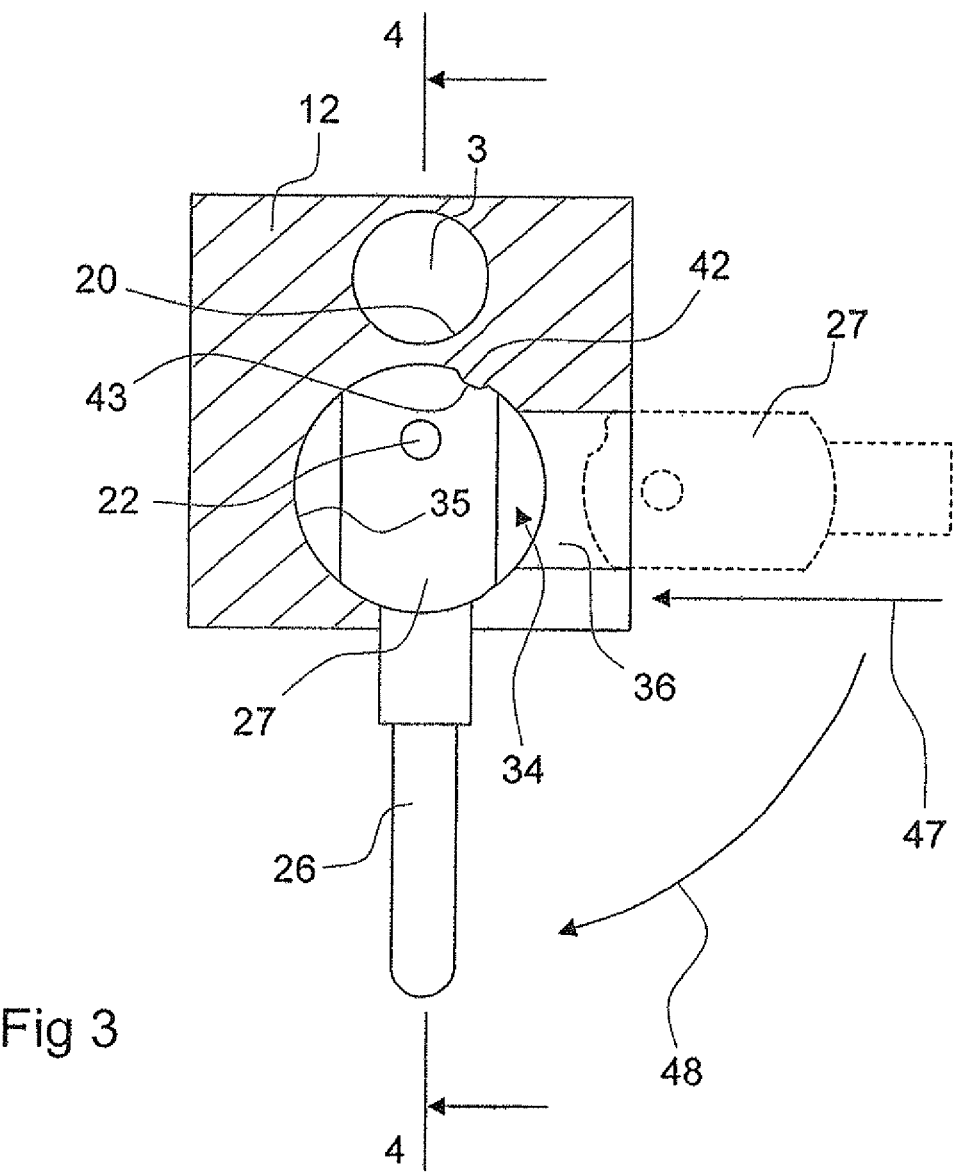
FIG. 3 shows a section according to Line 3-3 in FIG. 2, FIGS. 4A and 4B show a plug body according to exemplary embodiments.
Figure 3A:
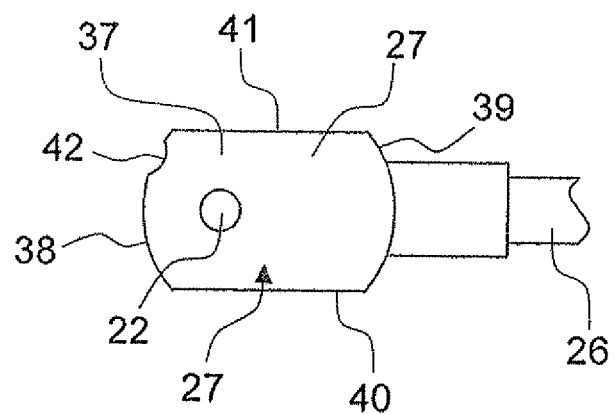
Figure 3B:
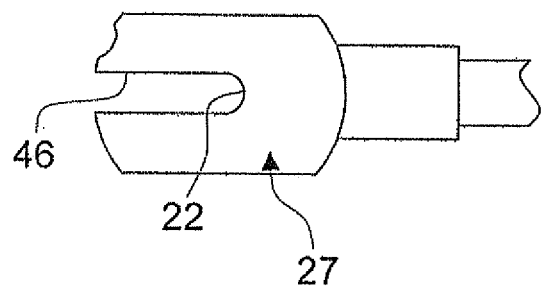
Figure 5:
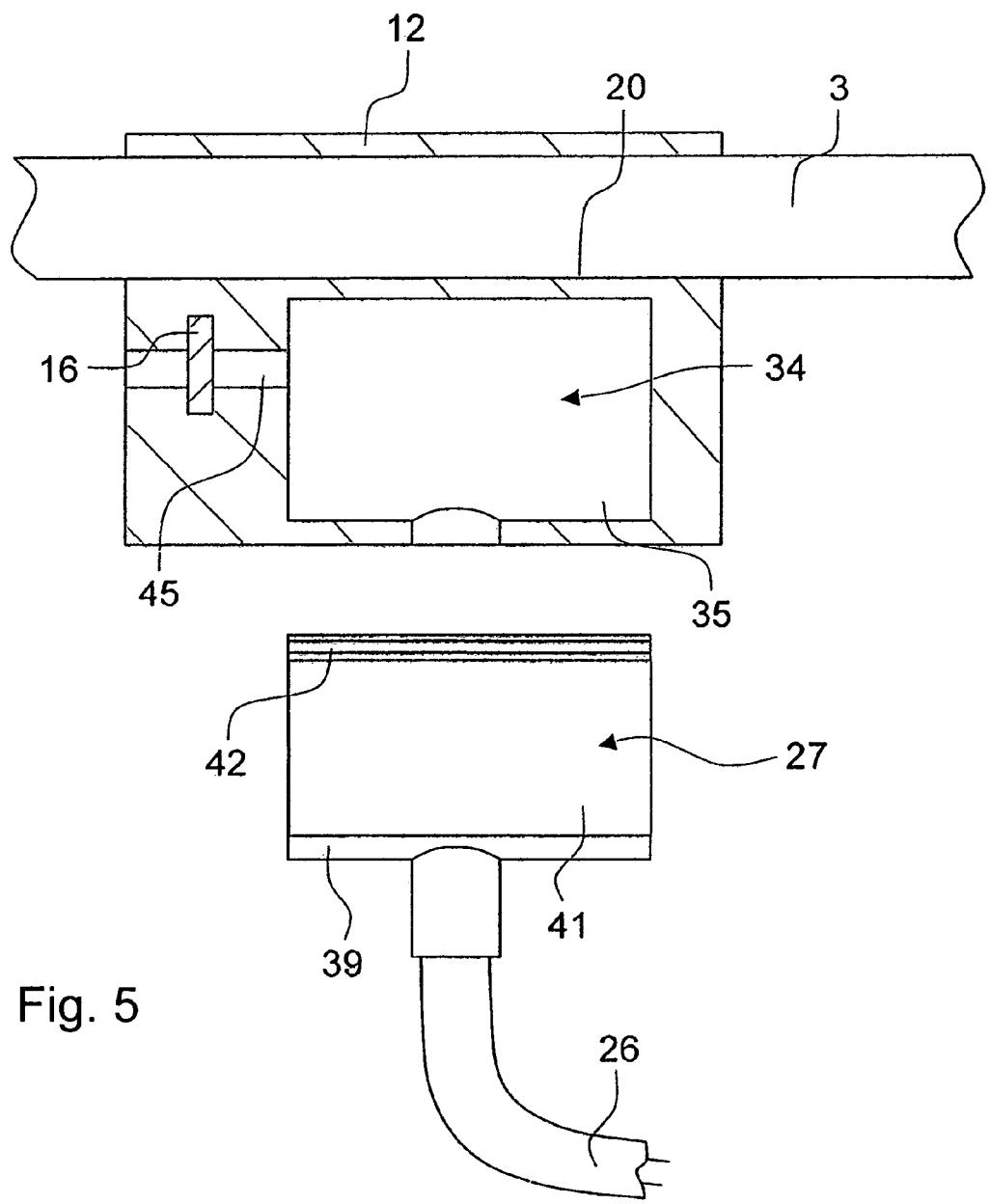
FIG. 5 shows a section according to Line 4-4 in FIG. 3.

A retaining body 12 in the form of a slide which can be moved in a longitudinal direction is mounted on the guide tube 3. FIGS. 3 and 5 show that the retaining body 12 is mounted on the guide tube 3 by means of a guide hole 20.

FIG. 1 shows that a spring 13 is arranged between the retaining body 12, which is mounted so that it can be moved in a longitudinal direction, and the guide plate 4, which is fixed with respect to the shaft tube 2. Handle pieces 14 and 15, which can be operated by the fingers of one hand and with which the retaining body 12 can be moved longitudinally against the force of the spring 13, are fixed on the holding body 12 and on the guide plate 4.

Figure 2:
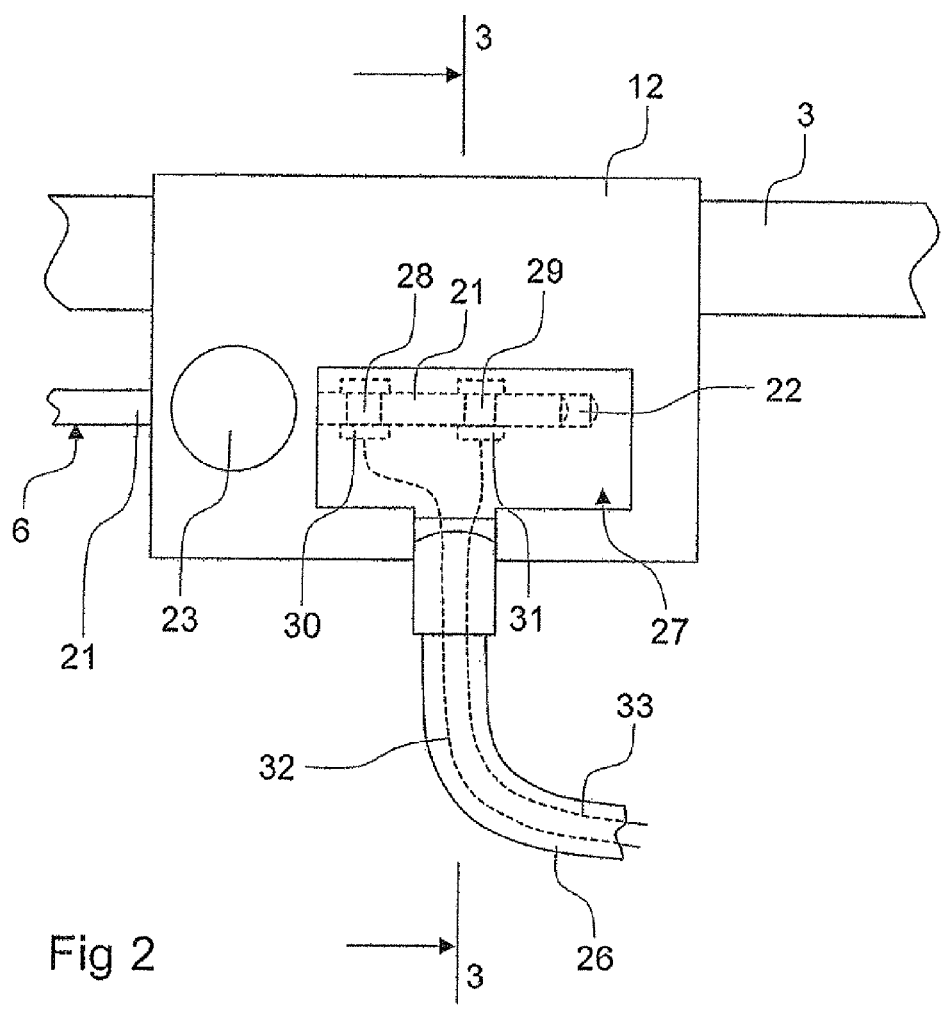
FIG. 2 shows an enlarged side view of FIG. 1 in the region of the retaining body.

FIG. 1 shows that, with the electrode 7, the electrode arrangement 6 runs from its distal end longitudinally through the shaft tube 2 and emerges therefrom proximally to run parallel to the guide tube 3 as far as the retaining body 12. FIG. 2 shows that a proximal end region 21 of the electrode arrangement 6 runs inside the retaining body 12 into an electrode mounting 22, which is designed in the form of a hole which is aligned parallel to the guide tube 3.

A slider 16 (FIG. 5), which is provided with an actuating knob 23 and is mounted in the retaining body 12 so that it can be moved at right angles to the guide rod 3, is provided with latching means (not shown), by means of which it can engage in a latching manner at the end region 21 of the electrode arrangement 6 to secure the latter in the electrode mounting 22 in the position shown in FIG. 2. By pressing the actuating knob 23, the slider 16 can be moved so that the catch is released and the electrode arrangement can be withdrawn from the retaining body 12. If the electrode arrangement is latched in the retaining body 12, then it can be moved thereby in the longitudinal direction under fine control in order to be able to carry out the required tissue cuts with the electrode 7.

In enlarged views of the retaining body 12, FIGS. 2 and 5 show that a plug body 27, which is attached to the end of a cable 26, is releasably inserted in said retaining body. In FIG. 2, the plug body 27 is shown in its end position in the retaining body 12. Here, the connection inside the plug body 27 can be seen dashed. Ring-shaped contact surfaces 28 and 29, which are electrically connected to the electrodes 7 and 10 by means of internal conductors in the electrode arrangement 6, are located on the end region 21 of the electrode arrangement 6. In the position of the end region 21 shown, the ring-shaped contact surfaces 28 and 29 make contact with contact rings 30 and 31 which are arranged in the plug body 27 and are thereby connected to conductors 32 and 33 through the cable 26. The cable 26 can be connected to the two poles of a bipolar current source in a manner which is not shown.

FIG. 3 shows a plug receptacle 34 in the retaining body 12 which is designed to accommodate the plug body 27. The plug receptacle 34 forms a cylinder chamber 35 which is formed inside the retaining body 12 and is accessible from the outside through a slot 36.

Figure 4A:
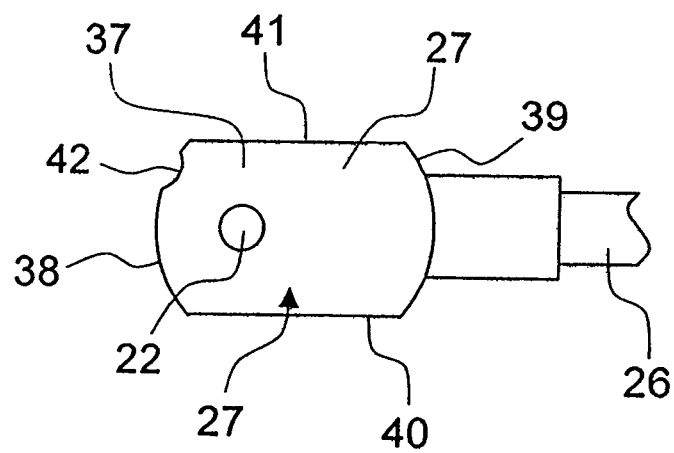

As FIG. 4A shows, the plug body 27 has a cylinder head 37 which is bounded by two cylinder surfaces 38, 39 and two parallel surfaces 40, 41. The cylinder surfaces 38, 39 are formed so that they can run in a sliding manner inside the cylinder chamber 35. The parallel surfaces 40, 41 are at a distance apart which is not greater than the height of the slot 36 and is less than the diameter of the cylinder chamber 35.

FIG. 3 shows that, in its position shown dashed in FIG. 3, the plug body 27 can be moved with an inserting movement into the slot 36 in the direction of the arrow 47. Here, it can be moved into the cylinder chamber 35 and can then be turned through 90° as shown by the arrow 48 into the position shown in which the cable 26 now hangs down.

In this position, the plug body 27 is retained in the retaining body 12 by interlocking, and can only be removed by turning back through 90° (in the opposite direction to arrow 48) and then withdrawing through the slot 36 (in the opposite direction to arrow 47). The plug body 27 can be secured against unintentional turning in the end position of the plug body 27 in the retaining body 12 shown in FIG. 3. On the one hand, the cable 26 which hangs down under gravity can be used for this purpose while the retaining body 12 is predominantly held so that, as FIG. 3 shows, the guide hole 20 is at the top. The cable 26 then hangs down under gravity and secures the plug body 27 in the end position shown.

FIG. 3 shows that a further possibility for securing the plug body 27 in the end position can be provided by means of a latching device. This is shown in FIG. 3. A longitudinal groove 42 is arranged on the cylinder surface 38. The cylinder chamber 35 has a rib 43 which projects inwards. In the rotational position of the plug body 27 corresponding to the end position, which is shown in FIG. 3, the rib 43 latches into the longitudinal groove 42, for which purpose the material of the retaining body 12 or of the plug body 27 is of appropriate elasticity.

A sprung ball, for example, which latches into the longitudinal groove 42, can also be provided instead of the rib 43. Other securing latching devices are possible at this point. For example, a clamp (not shown), into which the cable 26 can be latched in the position shown in FIG. 3, that is to say in the end position of the plug body 27, can be attached to the retaining body 12.

FIG. 5 shows the arrangement of FIG. 3 in the section according to Line 4-4. Here, the plug body 27 has been removed from the plug receptacle 34 and shown separately to improve clarity.

FIG. 1 shows that, in the region of the retaining body 12, the electrode arrangement 6 runs parallel to and at a distance from the guide tube 3. This distance should be as small as possible for a number of design reasons.

Therefore, as FIGS. 2 to 5 show, the electrode mounting 22 is not arranged on the cylinder axis of the cylinder surfaces 38 and 39 of the plug body 27 but is offset with respect thereto towards the guide hole 20. The parallel distance between them is thereby reduced.

FIG. 5 shows that, before being inserted into the electrode mounting 22 in the plug body 27, the end region 21 of the electrode arrangement 6 must pass through another hole 45 in the retaining body 12. This is only in line with the electrode mounting 22 in the plug body 27 in its end position and not in the position which is rotated through 90° in which the plug body 27 can be fed through the slot 36.

The result of this is that the end region 21 of the electrode arrangement 6 can only be inserted into the electrode mounting 22 in the plug body 27 when the plug body is in its end position.

Figure 4B:
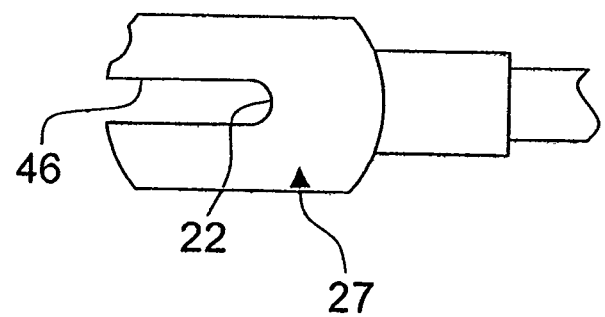

A plug body 27 is shown in FIG. 4B in an embodiment in which the electrode mounting 22 lies exactly on the cylinder axis of the cylinder surfaces 38 and 39. In this case, the hole 45 shown in FIG. 5 must of course also be appropriately offset.

This results in a somewhat less favorable, larger distance between the electrode arrangement 6 and the guide tube 3. However, a design option is then provided for opening the electrode mounting 22 on the outside by means of a slot 46. There is therefore the possibility here of first fitting the electrode arrangement and only then inserting the plug body 27. When the plug body 27 is inserted, the slot 46 slides over the end region 21 of the electrode arrangement 6, which is located centrally in the cylinder chamber 35 of the plug receptacle 34. The plug body 27 can then be rotated about the end region 21 which lies on the cylinder axis.

The invention claimed is:

1. A retaining body of a resectoscope, the retaining body comprising:
   a guide hole for mounting the retaining body on the resectoscope such that the retaining body can be moved in a direction along a longitudinal axis of the resectoscope;
   an electrode hole configured to accommodate a proximal end region of an electrode arrangement; and
   a plug receptacle comprising a chamber formed in the shape of a cylinder, the chamber being accessible from an exterior surface of the retaining body through a slot, the slot having a first side surface and a second side surface opposite to the first side surface that defines a slot width therebetween, and wherein the slot width is smaller than a diameter of the chamber,
   wherein the plug receptacle is configured to accommodate a plug body such that the plug body can be:
      (i) inserted into the plug receptacle by an insertion movement of the plug body relative to the retaining body that is in a first direction at a right angle to the direction of movement of the retaining body;
      (ii) removed from the plug receptacle by a movement away from the retaining body that is opposite to the first direction; and
      (iii) rotated in a direction about the longitudinal axis of the resectoscope to reach an end position at which movement of the plug body away from the retaining body in a second direction at a right angle to the direction of movement of the retaining body is blocked by the retaining body,
   wherein the plug body can only be rotated to reach the end position once the plug body is contained within the retaining body at an end of the insertion movement.

2. A cable/plug body of a resectoscope, which comprises:
   a plug body that is formed in the shape of a modified cylinder having an outer circumferential surface with (i) two flat parallel surfaces in parallel to a center longitudinal axis of the modified cylinder and (ii) curved surfaces joining the two flat parallel surfaces, the outer circumferential surface circumscribing the center longitudinal axis, the parallel surfaces being a distance apart from each other that is less than a diameter of the modified cylinder, and the plug body including an electrode mounting hole that is elongate in a direction parallel to the center longitudinal axis; and
   a cable connected to the plug body and extending therefrom,
   wherein the electrode mounting hole is offset radially from the center longitudinal axis in a direction that is away from the cable.

3. The cable/plug body of claim 2, wherein the plug body is configured so that an electrode is engaged in the plug body by inserting the electrode into the electrode mounting hole in the direction parallel to the center longitudinal axis.

4. The cable/plug body of claim 2, wherein the two flat parallel surfaces are elongate in the direction parallel to the center longitudinal axis.

5. A resectoscope comprising:
   an electrode arrangement having at least one electrode, the at least one electrode being designed for the application of high frequency and being connected to a corresponding at least one contact at a proximal end region of the electrode arrangement, the electrode arrangement being configured to move in a direction along a longitudinal axis of the resectoscope;
   a retaining body which is mounted on the resectoscope such that it can be moved in the direction along the longitudinal axis of the resectoscope, the retaining body comprising:
      an electrode hole configured to accommodate the proximal end region of the electrode arrangement; and
      a plug receptacle; and
   a cable having a plug body designed to fix the cable to the retaining body while making contact with the at least one contact,
      wherein the plug receptacle is configured to accommodate the plug body such that the plug body can be:
         (i) inserted into the plug receptacle by an insertion movement of the plug body relative to the retaining body that is in a first direction at a right angle to the direction of movement of the electrode arrangement;
         (ii) removed from the plug receptacle by a movement away from the retaining body that is opposite to the first direction; and
         (iii) rotated in a direction about the longitudinal axis of the resectoscope to reach an end position at which movement of the plug body away from the retaining body in a second direction at a right angle to the direction of movement of the electrode arrangement is blocked by the retaining body,
      wherein the plug body can only be rotated to reach the end position once the plug body is contained within the retaining body at an end of the insertion movement.

6. The resectoscope as claimed in claim 5, wherein:
   the plug body is formed in the shape of a modified cylinder having two flat parallel surfaces in parallel to a longitudinal axis of the modified cylinder, the parallel surfaces being a distance apart from each other that is less than a diameter of the modified cylinder; and
   the plug receptacle comprises a chamber formed in the shape of a cylinder having a diameter equal to the diameter of the modified cylinder, the chamber being accessible from an exterior surface of the retaining body through a slot which is narrower than the diameter of the modified cylinder and wider than the distance between the parallel surfaces.

7. The resectoscope as claimed in claim 5, wherein when the plug body is inserted into the plug receptacle, a longitudinal axis of the plug body is arranged parallel to the longitudinal axis of the resectoscope.

8. The resectoscope as claimed in claim 5, wherein the retaining body has a latching device which is designed to secure the plug body in the end position.

9. The resectoscope as claimed in claim 5, wherein the plug body comprises an electrode mounting for accommodating the proximal end region of the electrode arrangement, wherein the electrode mounting aligns with the electrode hole when the plug body is positioned at the end position.

10. The resectoscope as claimed in claim 9, wherein:
    the retaining body further comprises a guide hole for mounting the retaining body on the resectoscope; and
    the electrode mounting is designed in the form of a hole which is arranged parallel to the longitudinal axis of the plug body and lies closer to the guide hole than to the longitudinal axis of the plug body when the plug body is positioned at the end position.

* * * * *